United States Patent
Mathias et al.

(10) Patent No.: US 9,498,616 B2
(45) Date of Patent: *Nov. 22, 2016

(54) IRREVERSIBLY CLOSABLE FLOW CONTROL CLAMP

(71) Applicant: Fenwal, Inc., Lake Zurich, IL (US)

(72) Inventors: Jean-Marie Mathias, Gesves (BE); Gianni DiStefani, Ath (BE)

(73) Assignee: Fenwal, Inc., Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/601,416

(22) Filed: Jan. 21, 2015

(65) Prior Publication Data

US 2015/0133876 A1    May 14, 2015

Related U.S. Application Data

(63) Continuation of application No. 13/196,668, filed on Aug. 2, 2011, now Pat. No. 8,956,339, which is a continuation of application No. 12/401,332, filed on Mar. 10, 2009, now Pat. No. 8,517,970, which is a continuation of application No. 10/501,571, filed as application No. PCT/US03/01758 on Jan. 21, 2003, now abandoned.

(60) Provisional application No. 60/353,930, filed on Jan. 31, 2002.

(51) Int. Cl.
*A61M 37/00* (2006.01)
*A61M 39/28* (2006.01)
*F16K 7/06* (2006.01)

(52) U.S. Cl.
CPC ............ *A61M 39/284* (2013.01); *F16K 7/063* (2013.01)

(58) Field of Classification Search
CPC ...... A61M 39/281–39/288; F16K 7/06–7/068
USPC .................................................. 604/403–416
See application file for complete search history.

(56) References Cited

U.S. PATENT DOCUMENTS

| | | |
|---|---|---|
| 2,722,932 A | 11/1955 | Hickey |
| 2,908,476 A | 10/1959 | Hidding |
| 2,950,716 A | 8/1960 | Walter et al. |
| 3,127,892 A | 4/1964 | Bellamy, Jr. et al. |
| 3,942,228 A | 3/1976 | Buckman et al. |
| 4,038,726 A | 8/1977 | Takabayashi |

(Continued)

FOREIGN PATENT DOCUMENTS

| | | |
|---|---|---|
| EP | 0206997 | 12/1986 |
| EP | 0691139 A1 | 1/1996 |

(Continued)

OTHER PUBLICATIONS

International Search Report for PCT/US03/01758 dated Jun. 23, 2003.

(Continued)

*Primary Examiner* — Philip R Wiest
(74) *Attorney, Agent, or Firm* — Cook Alex Ltd.

(57) ABSTRACT

A flow control clamp having a first member and a second member movable from a first open position to a second irreversibly closed position wherein flow through a tube associated with the clamp is irreversibly prevented and cannot be restored. Systems and methods using such clamps are also disclosed.

13 Claims, 4 Drawing Sheets

(56) References Cited

U.S. PATENT DOCUMENTS

| | | |
|---|---|---|
| 4,053,135 A | 10/1977 | Saliaris |
| 4,097,020 A | 6/1978 | Sussman |
| 4,193,174 A | 3/1980 | Stephens |
| 4,235,412 A | 11/1980 | Rath et al. |
| 4,247,076 A | 1/1981 | Larkin |
| 4,453,295 A | 6/1984 | Laszczower |
| 4,589,626 A | 5/1986 | Kurtz et al. |
| 4,643,389 A | 2/1987 | Eison et al. |
| 4,676,476 A | 6/1987 | Herrli |
| 4,725,269 A | 2/1988 | Danby et al. |
| 4,764,996 A | 8/1988 | Pino |
| 4,807,622 A | 2/1989 | Ohkaka et al. |
| 4,835,824 A | 6/1989 | Durham et al. |
| 4,857,274 A | 8/1989 | Simon |
| 4,988,355 A | 1/1991 | Leveen et al. |
| 5,035,399 A | 7/1991 | Rantanen-Lee |
| 5,062,846 A | 11/1991 | Oh et al. |
| 5,167,656 A | 12/1992 | Lynn |
| 5,203,056 A | 4/1993 | Funk et al. |
| 5,226,892 A | 7/1993 | Boswell |
| 5,238,218 A | 8/1993 | Mackal |
| 5,270,003 A | 12/1993 | Bernes et al. |
| 5,416,954 A | 5/1995 | Sobin |
| 5,615,965 A | 4/1997 | Saurat et al. |
| 5,651,766 A | 7/1997 | Kingsley et al. |
| 5,702,383 A | 12/1997 | Giesler et al. |
| 5,817,116 A | 10/1998 | Takahashi et al. |
| 5,827,306 A | 10/1998 | Yoon |
| 5,836,619 A | 11/1998 | Shemesh et al. |
| 5,928,166 A | 7/1999 | Shemesh et al. |
| 6,089,527 A | 7/2000 | Utterberg |
| 6,113,062 A | 9/2000 | Schnell et al. |
| 6,123,859 A | 9/2000 | Lee et al. |
| 6,126,618 A | 10/2000 | Bischof |
| 6,132,407 A | 10/2000 | Genese et al. |
| 6,161,812 A | 12/2000 | Guala et al. |
| 6,193,675 B1 | 2/2001 | Kraus et al. |
| 6,234,448 B1 | 5/2001 | Porat |
| 6,238,377 B1 | 5/2001 | Liu |
| 6,298,526 B1 | 10/2001 | Baumdicker et al. |
| 6,328,726 B1 | 12/2001 | Ishida et al. |
| 6,387,086 B2 | 5/2002 | Mathias et al. |
| 6,553,632 B1 | 4/2003 | Brumpton |
| 6,592,613 B1 | 7/2003 | Ishida |
| 6,626,884 B1 | 9/2003 | Dillon et al. |
| 6,638,282 B2 | 10/2003 | Ramsey |
| 6,644,618 B1 | 11/2003 | Balbo |
| 6,692,479 B2 | 2/2004 | Kraus et al. |
| 6,708,931 B2 | 3/2004 | Miura |
| 6,730,071 B1 | 5/2004 | Dassa |
| 6,742,760 B2 | 6/2004 | Blickhan et al. |
| 6,923,792 B2 | 8/2005 | Staid et al. |
| 7,044,941 B2 | 5/2006 | Mathias et al. |
| 7,087,047 B2 | 8/2006 | Kraus et al. |
| 7,137,611 B2 | 11/2006 | Aulicino |
| 7,384,416 B2 | 6/2008 | Goudaliez et al. |
| 7,766,854 B2 | 8/2010 | Goudaliez et al. |
| 8,262,639 B2 | 9/2012 | Mathias |
| 8,517,970 B2 * | 8/2013 | Mathias et al. ............... 604/6.15 |
| 8,956,339 B2 * | 2/2015 | Mathias et al. ............... 604/403 |
| 2004/0106890 A1 | 6/2004 | Goudaliez et al. |
| 2005/0038374 A1 | 2/2005 | Williams, Jr. et al. |
| 2005/0107765 A1 | 5/2005 | Kashmiran et al. |
| 2005/0171492 A1 | 8/2005 | Rodriquez |
| 2006/0015074 A1 | 1/2006 | Lynn |
| 2006/0129170 A1 | 6/2006 | Royce et al. |
| 2007/0007208 A1 | 1/2007 | Brugger et al. |
| 2007/0161978 A1 | 7/2007 | Fedenia et al. |
| 2007/0219513 A1 | 9/2007 | Lina et al. |

FOREIGN PATENT DOCUMENTS

| | | |
|---|---|---|
| EP | 0799627 A | 10/1997 |
| EP | 1000633 | 5/2000 |
| EP | 1064959 A | 1/2001 |
| EP | 1125596 A | 8/2001 |
| EP | 03703927 | 3/2005 |
| WO | WO93/25143 A | 12/1993 |
| WO | WO00/77428 A2 | 12/2000 |
| WO | WO01/08582 A1 | 2/2001 |
| WO | WO03/063945 A1 | 8/2003 |
| WO | WO2007/112500 | 10/2007 |
| WO | WO2007/133291 | 11/2007 |

OTHER PUBLICATIONS

Supplemental International Search Report for EP 03703927 dated Mar. 30, 2005.
Extended European Search Report and Opinion for EP 09015333 dated Jun. 30, 2010.
U.S. Appl. No. 12/371,210, filed Feb. 13, 2009.
U.S. Appl. No. 12/371,247, filed Feb. 13, 2009.
Extended European Search Report for EP Application No. EP 10 009215 dated Jul. 11, 2011.
Photographs of Baxter "All in One Container" and Instruction Sheet dated Sep. 2001.

* cited by examiner

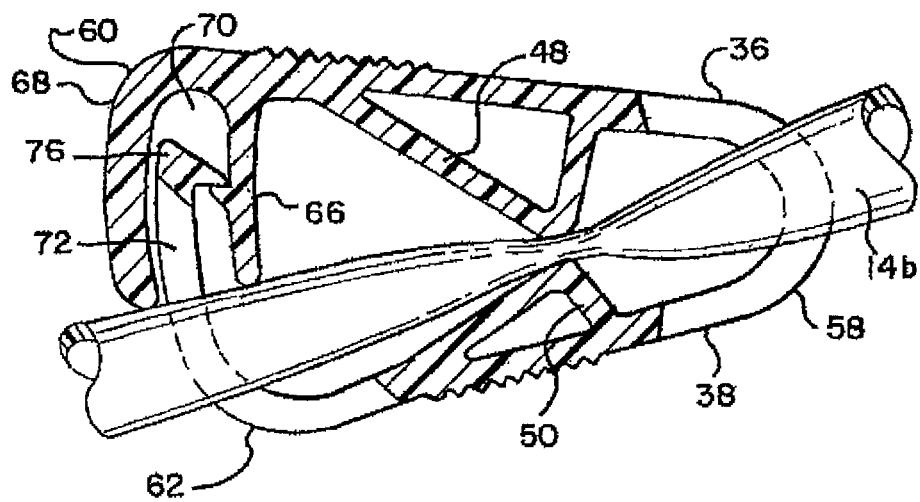
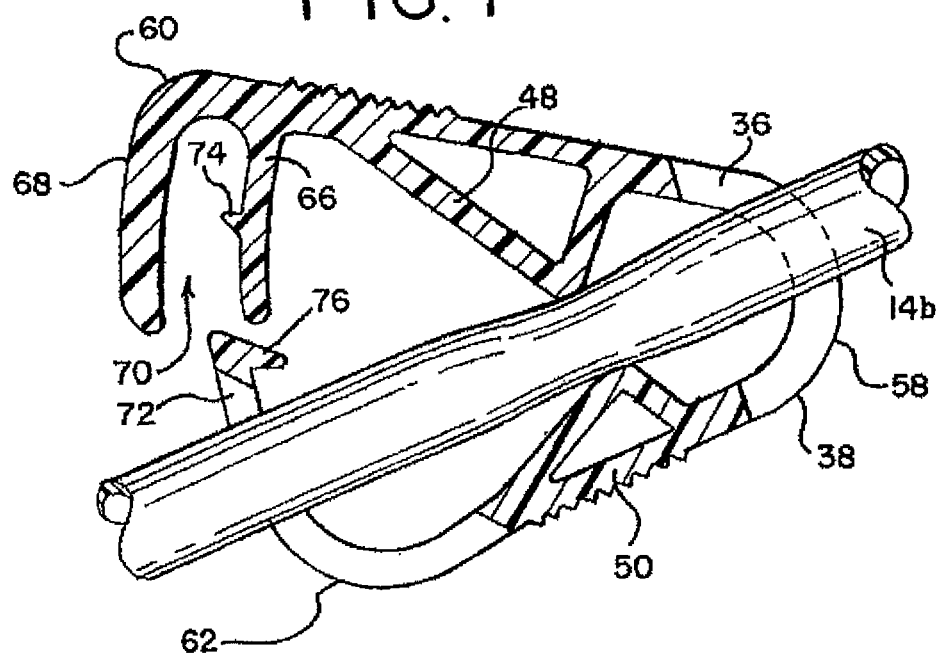

IRREVERSIBLY CLOSABLE FLOW CONTROL CLAMP

RELATED APPLICATIONS

This application is a continuation of application U.S. patent application Ser. No. 12/401,332, filed on Mar. 10, 2009, which is a continuation of U.S. patent application Ser. No. 10/501,571, filed on Apr. 27, 2005, which is a national stage entry of International Application No. PCT/US03/01758, filed on Jan. 21, 2003 and designating the United States, and claims the benefit of U.S. Provisional Patent Application Ser. No. 60/353,930, filed on Jan. 31, 2002, which applications are incorporated by reference herein.

The present application relates to clamps for controlling the flow of liquid through a flexible tube. More particularly, the present invention relates to flow control clamps that can be substantially irreversibly secured in a closed position, thereby discouraging reopening of the flow path of the tube.

BACKGROUND OF THE INVENTION

A disposable plastic container and tubing set or fluid circuit is typically used for collecting blood from a donor. The disposable blood collection set includes a venipuncture needle for insertion into the arm of the donor. The needle is attached to one end of a flexible plastic tube which provides a flow path for the blood. The other end of the plastic tube is attached to one or more plastic bags or containers for collecting the withdrawn blood.

The blood collection set may also include a sampling sub-unit. The sampling sub-unit allows for collection of a sample of blood, which sample can be used for testing of the blood. Preferably, the sample is obtained prior to the "main" collection of blood. Collecting the sample prior to the main collection reduces the risk that bacteria residing on the donor's skin where the needle is inserted (i.e., in particular, the small section of detached skin commonly referred to as the "skin plug") will not enter the collection container and contaminate the blood collected for transfusion. Thus, it is preferred that the blood samples which may include the skin plug, be diverted from the main collection container.

An example of a blood collection set with such a "pre-donation" sampling sub-unit is described in U.S. patent application Ser. No. 09/364,628 filed Jul. 29, 1999, and U.S. patent application Ser. No. 09/492,060 filed Jan. 27, 2000, which are incorporated by reference herein. The collection sets described therein include a needle and a length of tubing, one end of which is attached to the needle and the other end of which is attached to one or more collection containers. The tubing set also includes an additional line which is branched from the main line at a Y-connection site in the tubing set. The branched line is attached to a sampling pouch for collecting a smaller volume of blood from which samples may be obtained.

The sampling sub-unit may further include a pre-attached holder for receiving blood sample vials or tubes. The holder is connected to the outlet port of the sampling pouch and includes a needle in the holder interior. When the blood sample vial is inserted into the holder, the needle pierces the rubber cap (septum) of the vial and blood from the sampling pouch is drawn into the vial. The blood-filled vial is removed from the holder and the procedure may be repeated with as many vials as required.

The blood collection set described above also includes flow control clamps for controlling the flow of biological fluid (e.g., blood) through the set and to the sampling pouch and/or collection container. Flow control clamps commonly used are the Roberts-type clamps, which are well known in the art. The Roberts-type clamps are placed on the tubing line leading to the blood collection container and on the tubing line leading to the sampling pouch. A Roberts-type clamp is typically made from a strip of plastic. The ends of the strip are curved toward each other to provide two "legs" which are adapted to engage each other in a snap-fit, spring relation. The body of the clamp includes a pair of apertures through which the tubing passes.

The clamp further includes a pair of projections or tube contacting members which compress the tubing when the body of the clamp is depressed, thereby restricting flow, through the tube. Clamps of this type are generally described in U.S. Pat. Nos. 3,942,228, 6,089,627 and 6,113,062, all of which are incorporated herein by reference.

The clamps described in these patents also typically include means for locking the legs together and release means which, when actuated by the technician, disengages the locked legs of the flow control clamp. Disengagement of the ends decompresses the tube and permits fluid flow through the flow path. Thus, by selectively opening and closing the different flow paths (by depressing or releasing the clamps), the technician can control the flow of blood from the donor, diverting the blood to the desired container or sampling pouch, as necessary.

In certain instances, however, it may not be desirable to reopen a closed flow path. This may particularly be the case when drawing blood samples from the sampling pouch into sample vials. For example, when the sampling pouch is filled with the required or desired volume of blood (for sampling), the line from the donor to the pouch is typically closed by the Roberts-type clamp, and remains closed as the sampling vials are filled. After clamping the sampling line closed, technicians are further instructed to more permanently seal the line using metal clips or by heat-sealing the line in ways that will be known to those in the field. Sealing the sampling line substantially ensures that airborne bacteria or other contaminants that may enter the set through the sampling sub-unit do not contaminate the remainder of the set, including the needle and tube leading to the collection container. In short, the clips or heat seal provide a sterile barrier to the remainder of the set.

Unfortunately, on occasion, prior to permanently sealing the sampling line, some technicians have been known to unclamp the sampling line in order to draw additional blood into the pouch so that additional sample vials may be filled. However, by doing so, the system becomes "open" and contaminants introduced from the outside environment may enter the system. Current flow control clamps are readily and easily openable, and do not provide a disincentive to drawing additional blood into the sampling pouch. If the clamp could not be so readily released from the closed position, the technician would not have the option of reopening the line but would, hopefully, proceed with permanently sealing the line to form the sterile barrier. Accordingly, it would be desirable to provide a clamp that discourages and substantially prevents the reopening of the sampling or other blood tube line.

SUMMARY OF THE INVENTION

In one aspect, the present invention is directed to a flow control clamp that includes a flexible body. The body has a first leg and a second leg disposed in a generally facing relationship. The legs are moveable between a first spaced apart position and closed position. The clamp includes two apertures in the body for receiving a flexible tube therethrough and between the legs. The clamp further includes at least one tube contacting member carried by one of the legs for clamping the tube when the legs are in the closed position. The first and second legs include surfaces disposed to irreversibly secure the legs together in the closed position.

BRIEF DESCRIPTION OF THE DRAWINGS

FIG. 7 is a cross-sectional, side view of the flow control clamp embodying the present invention in the open position;

FIG. 8 is a cross-sectional, side view of the flow control clamp embodying the present invention in the irreversibly locked position;

DETAILED DESCRIPTION OF THE DRAWINGS

Figure 1:
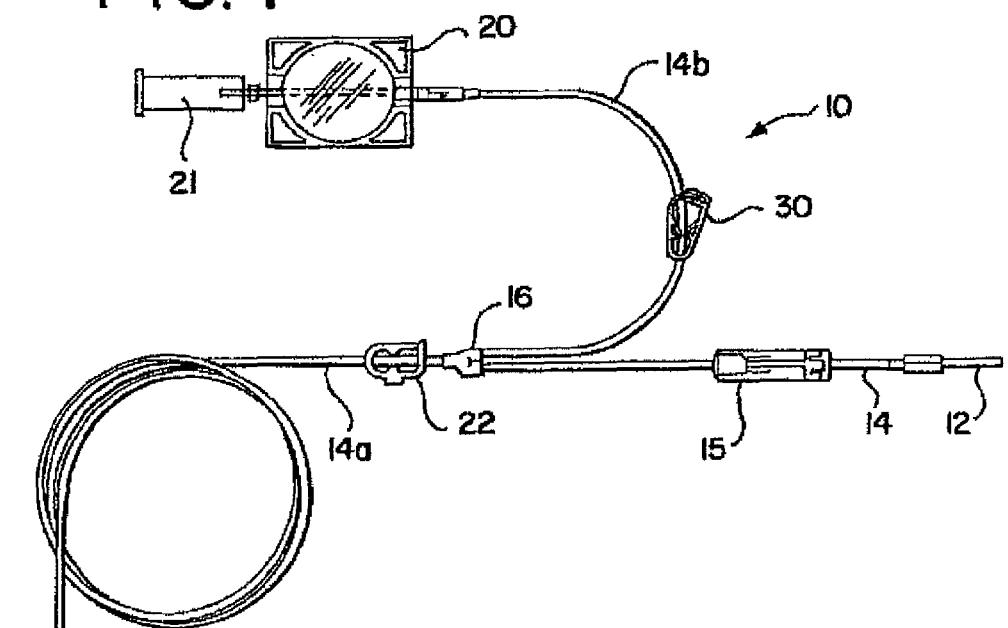
FIG. 1 is a perspective view of a blood tubing set including a flow control clamp embodying the present invention.

Turning now to the drawings, FIG. 1 depicts a blood collection set 10 of known type that is used in the collection of blood from a donor. Tubing set 10 includes a venipuncture needle 12 and a length of tubing 14. Tubing 14 branches at Y-connector 16 into tubing segment 144 and tubing segment 14b. Tubing segment 14a provides a flow path to a collection container 18 and tubing segment 14b provides a flow path to a sampling pouch 20. The sampling pouch may also include a holder 21 for receiving a blood sampling vial or tube. (Also shown is a needle protector 16 for storing the needle after use.)

In the blood tubing sets of the type shown in FIG. 1, tubing segments 14a and 14b are passed through flow control clamps 22 and 30 which may be a standard Roberts-type clamp and an irreversibly closable flow control clamp embodying the present invention. As used herein, the terms irreversibly closed or closable means that the flow control clamp, once in the closed position, is not readily releasable from the closed position in the normal and intended mode of operation. An "irreversibly" closed or closable flow control clamp can only be released from the closed and locked position by extraordinary and unintended manipulation of the clamp, including breakage of the clamp. A flow control clamp that is "irreversibly" closed or closable includes no release members such as, but not limited to, those described in U.S. Pat. Nos. 3,942,228, 6,089,527, 6,113,062.

Thus, whereas flow control clamp 22 can be selectively opened and closed, as desired, clamp 30, made in accordance with the present invention, once closed, remains irreversibly closed.

Figure 2:
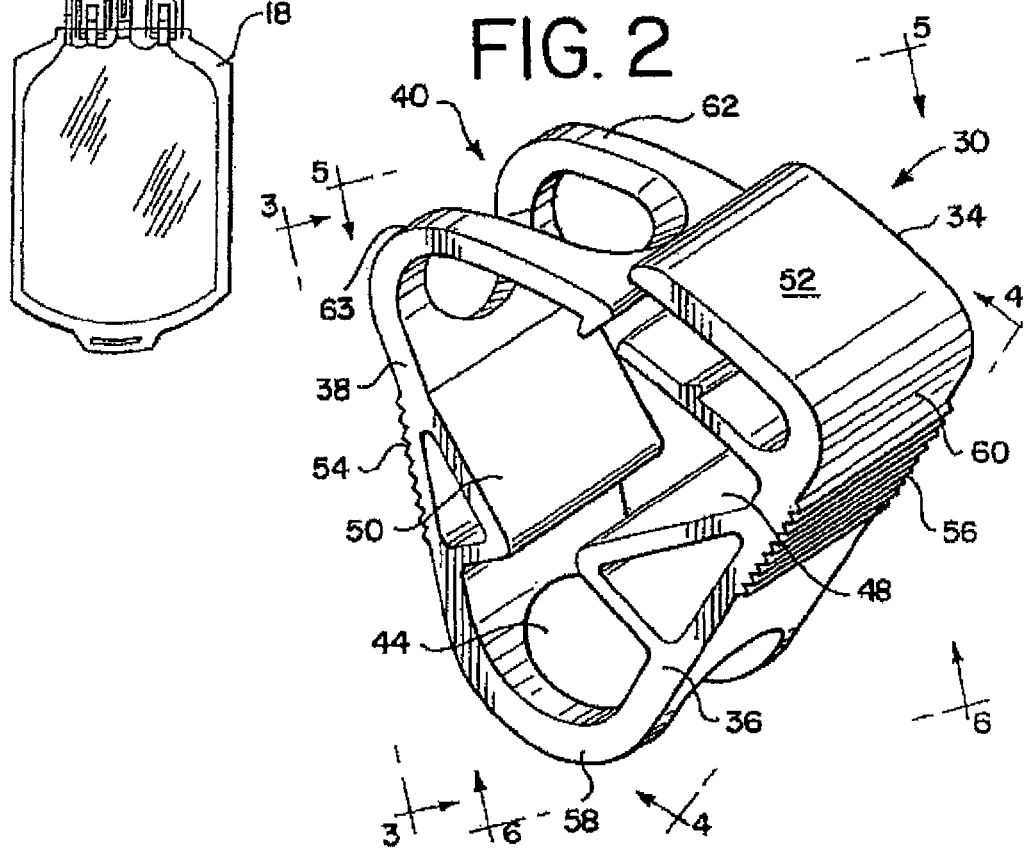
FIG. 2 is a perspective view of a flow control clamp embodying the present invention.

Turning now to FIG. 2, flow control clamp 30 of the present invention includes a generally curved, bent or otherwise non-linear body 34 (described in more detail below). Preferably, flow control clamp 30 may be made of any flexible, moldable, plastic material that can be steam sterilized. In addition, flow control clamp 30 and body 34 should be made of a material that is strong, yet sufficiently flexible so that the clamp can be flexed and squeezed by the technician without breaking. Examples of suitable materials are many, of the known plastic materials typically used in the medical field, including, but not limited to polyoxymethylene and polypropylene. Most preferred of the above-identified materials is polyoxymethylene, such as the polyoxymethylene known as Hostaform™ available from Ticona of Frankfurt, Germany. In addition, other materials that can be sterilized by other forms of sterilization, such as gamma sterilization, may also be used. One such material is a terpolymer of acrylonitrile, butadiene and styrene (ABS).

As further shown in FIG. 2, flow control clamp 30 includes body 34 that has two legs 36 and 38. Legs 36 and 38 are disposed in a generally facing relationship relative to each other. Legs 36 and 38 are initially in a spaced apart position as shown in FIG. 7, and are movable from the spaced apart position toward each other and to a closed position.

Body 34 further includes apertures 40 and 44 for receiving a length of plastic tubing therethrough. As shown in FIG. 2, apertures 40 and 44 are preferably circular or oval-like and are entirely contained within body 34 of flow control clamp 30. Thus, when a length of tubing 43 is inserted through apertures 40 and 44, the apertures completely enclose and surround the tubing at the point where the tubing extends through the apertures. Also, it may be preferable that apertures 40 and 44 be generally aligned with each other and not substantially offset relative to one another. This provides, among other things, for easier threading of the length of tubing 43. Alternatively, apertures need not completely surround the tube, but instead may include lateral slots, as described, for example, in U.S. Pat. No. 6,113,062. The lateral slots extend to the outer edge of the body so that during insertion of the tube, the clamp can be laterally slipped on the tube (as opposed to threading).

Flow control clamp 30 includes one or more tube contacting members 48 and 50. Tube contacting members 48 and 50 are carried by legs 36 and 38, respectively. As shown in FIG. 2, tube contacting members 48 and 50 may be teeth-like projections which compress the tubing when the clamp is closed. Alternatively, tube contacting members 48 and 50 may simply be blunt, oppositely facing surfaces. Although two oppositely facing contacting members are shown in FIG. 2 and are preferred, it will be understood that flow control clamp 30 of the present invention may include only one tube contacting member carried by one of the legs 36 or 38.

Figure 3:
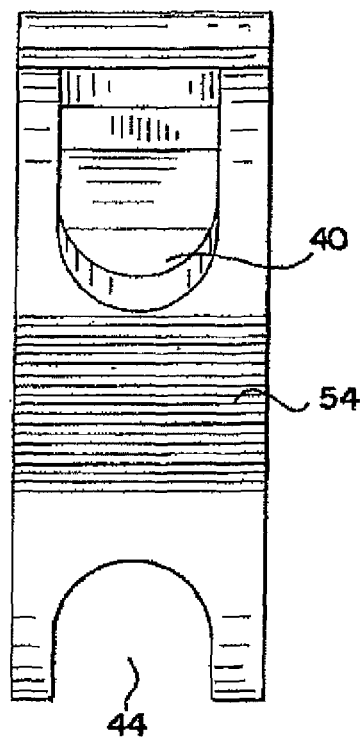
FIG. 3 is a plan view of the flow control clamp of FIG. 2 taken from lines 3-3 of FIG. 2.
Figure 4:
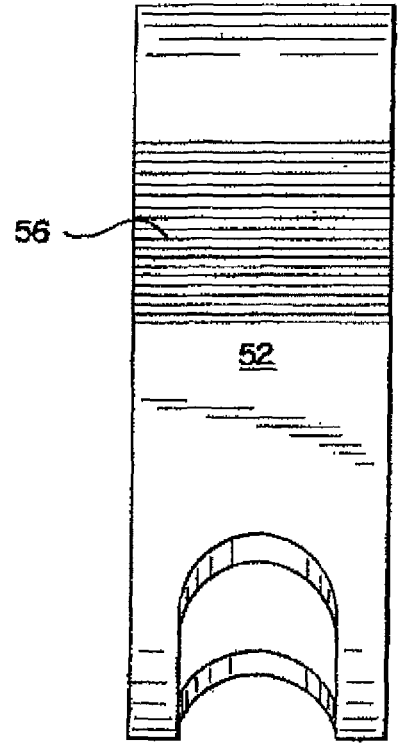
FIG. 4 is a plan view of the flow control clamp of FIG. 2 taken from lines 4-4 of FIG. 2.
Figure 5:
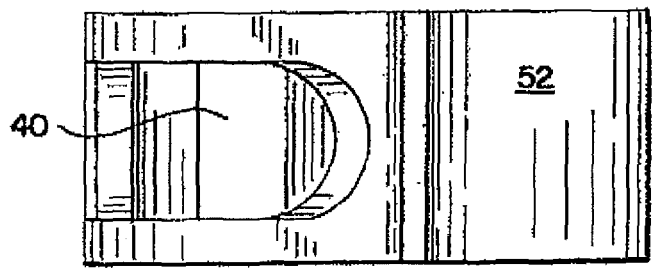
FIG. 5 is a plan view of the flow control clamp of FIG. 2 from lines 5-5.
Figure 6:
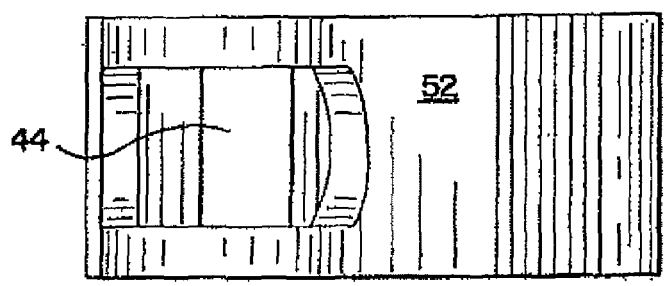
FIG. 6 is a plan view of the flow control clamp of FIG. 2 taken from lines 6-6.

The outer surface 52 of flow control clamp 30 is generally flat and smooth. However, outer surface 52 may include members that are roughened or textured to provide some friction when contacted by the fingertips of the technician during operation. As shown in FIGS. 3 and 4, outer surface 52 of body 34 includes ribbed members 54 and 56, which provide such a frictional surface for contacting by the fingers of the technician during closure and compression of flow control clamp 30.

As best shown in FIGS. 7 and 8, flow control clamp 30 is substantially free of any sharp corners or edges. For example, bends 58, 60 and 62 in body 34 are not abrupt, sharp corners, but are gradually curved and rounded. In addition, edges 63 of body 34 are preferably rounded or beveled. A flow control clamp 30 that is substantially free of sharp corners and edges and is more rounded or beveled, like the flow control clamp shown in FIGS. 7 and 8, ensures that the flow control clamp will not puncture the packaging of blood processing sets, thereby maintaining sterility of the packaged set.

As discussed generally above, where the blood processing set includes a sampling pouch of the type shown in FIG. 1, it may be desirable to provide a flow control clamp 30 that provides an additional level of sterility maintenance by discouraging and perhaps even preventing the technician from reopening a previously closed clamp. This way, the sterility of the remainder of the blood processing set will be maintained and will not be compromised by bacteria from the outside environment.

Accordingly, flow control clamp 30, and more particularly, legs 36 and 38 include surfaces that are disposed for irreversibly securing together legs 36 and 38 when the legs of flow control clamp 30 are moved from a spaced-apart position to the closed position, as shown in FIGS. 7 and 8.

Many different means for securing legs 36 and 38 together in a way that prevents easy reopening by the technician are contemplated by the present invention. For example, flow control clamp 30 may include means on the leg surfaces for interlocking legs 36 and 38. Specifically, as shown in FIGS. 7 and 8, leg 36 of flow control clamp 30 may include a pair of spaced-apart walls 66 and 68. Spaced-apart walls 66 and 68 define a slot 70 for receiving an extension 72 carried by leg 38. One of the spaced-apart walls 66 or 68 may further include a lip 74 that projects into slot 72, while the extension 72 includes a hook 76 that projects toward the wall 66.

As the legs 36 and 38 are moved from the spaced-apart position, as generally depicted in FIG. 7, to the closed position, tube contacting members 48 and 50 compress the tube 43, thereby restricting flow therethrough. As flow control clamp 30 is compressed further, extension 72 is outwardly displaced by wall 66 and enters slot 70. As hook 76 contacts lip 74, extension 72 is again outwardly displaced until it clears lip 74. Once clear of lip 74, extension 72 snaps forward toward wall 66, and hook 76 engages lip 74 to effectively close and lock flow control clamp 30.

Wall 68 prevents release or further outward displacement of extension 72 from the closed position, thereby resulting in an "irreversibly closed" flow control clamp 30. As shown in FIG. 8, wall 68 is a thicker and a less flexible wall than, for example, wall 66, thereby providing more strength to wall 68 and making it even more difficult to release extension 72. As will be appreciated by those in the field, flow control clamp 30 does not include any tabs or other means for readily releasing extension 72. Thus, flow control clamp 30 remains in the closed position.

Figure 9:
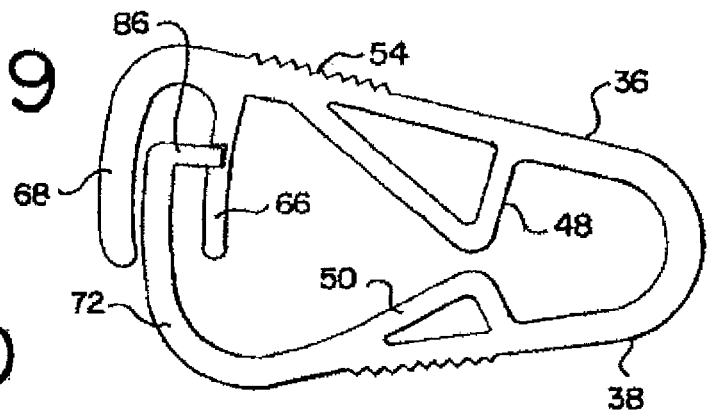
FIG. 9 is a side view of an alternative embodiment of the flow control clamp of the present invention.

FIGS. 9-12 include additional means for securing legs 36 and 38 in an "irreversibly closed" position. For example, as shown in FIG. 9, extension 72 may include a peg, and wall 66 includes a mating notch 84 for receiving peg 86 of extension 72. Extension 72 enters slot 70 in the manner generally described above, until peg 86 snaps into notch 84. Wall 68 again prevents outward movement of extension 72, thereby retaining flow control clamp 30 in an "irreversibly closed" position.

Figure 10:
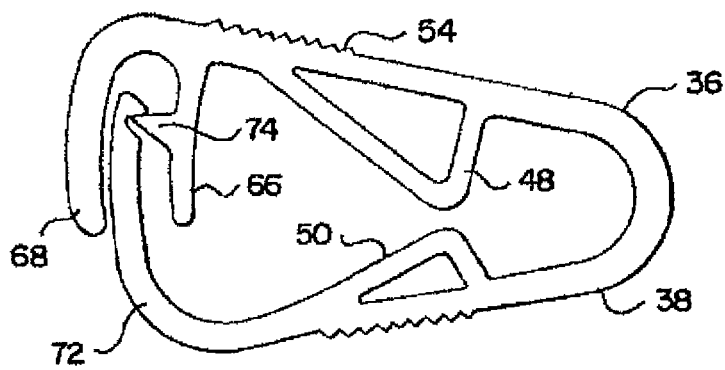
FIG. 10 is a side view of another alternative embodiment of the flow control clamp of the present invention.
Figure 11:
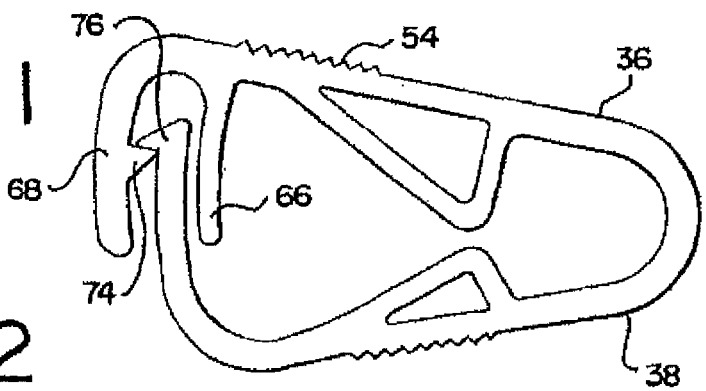
FIG. 11 is a side view of another alternative embodiment of the flow control clamp of the present invention.

FIG. 10 is an alternative embodiment where extension 72 includes a notch for receiving lip 74 of wall 66. In FIG. 11, lip 74 is located on wall 68 and is engaged by hook 76, as previously described.

Figure 12:
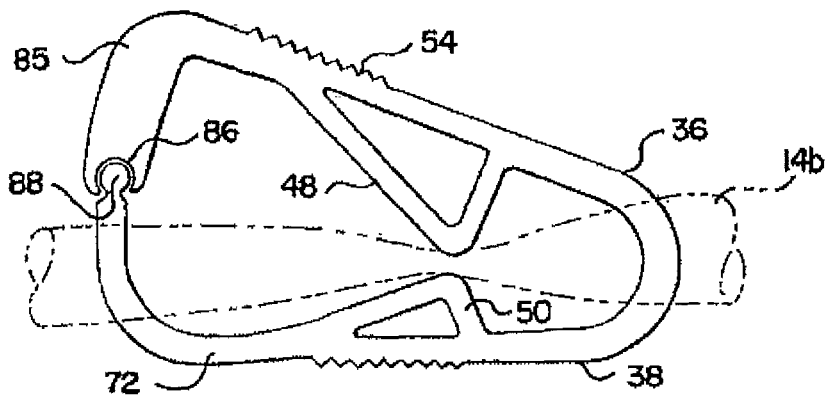
FIG. 12 is a side view of another alternative embodiment of the flow control clamp of the present invention.

FIG. 12 shows yet another alternative embodiment of the flow control clamp 30 of the present invention wherein leg 36 includes a single wall 85 projecting toward the interior (i.e., toward leg 38) of the flow control clamp 30. Leg 38 includes an extension, likewise, projecting toward the interior (i.e., and toward leg 36) of the flow control clamp 30. In order to secure legs 36 and 38 in the "irreversibly closed" position, one of the legs may include a socket 86, and the other of the legs may include a ball 8B for insertion into socket 86. This way, as in the previous embodiments, flow control clamp 30 may be closed or locked in the "irreversibly closed" position.

It will be appreciated that the description set forth above has been offered for illustrative purposes only. Other embodiments and other modifications to the flow control clamp shown and described above may also be included within the scope of the present invention. The above description is not intended to limit the scope of the invention of this application, which is as defined in the claims below.

The invention claimed is:

1. A flow control device comprising:
a body having a first leg and a second leg, said legs being movable from a first spaced apart position to a second irreversibly closed position wherein one of said first and second legs includes in an inwardly extending member having an engagement member and the other of said first and second legs includes a pair of inwardly extending members, one of said pair of inwardly extending members including a first surface engaged by said engagement member when said device is in said second irreversibly closed position and the other of said pair of inwardly extending members limits movement of said inwardly extending member having said engagement member away from said first surface and prevents disengagement of said engagement member from said engagement surface;
at least one opening provided in said body for receiving a tubing segment therethrough and between said legs; and
at least one tube contacting member carried by one of said legs for clamping said tubing segment when said legs are in the second irreversibly closed position.

2. The device of claim 1 wherein said pair of inwardly extending members define a space therebetween, whereby movement of said legs from said spaced apart position to said irreversibly closed position introduces said inwardly extending member having said engagement member into said space.

3. The device of claim 2 wherein said body is made of a polymeric material selected from the group consisting of polyoxymethylene and polypropylene.

4. The device of claim 2 wherein said first leg comprises a lip for said engagement member for engaging the first surface of one of the pair of inwardly extending members of the second leg when the device is in said irreversibly closed position.

5. The device of claim 2 wherein one of said pair of inwardly extending members is more rigid than said other of said pair of inwardly extending members.

6. The device of claim 1 further comprising a tube contacting member carried by the other of said legs being spaced and separate from said pair of inwardly extending members for clamping said tubing segment between said contacting members when said legs are in the second irreversibly closed position.

7. The device of claim 6 wherein the body defines a closed end where the first and second legs connect to each other, and at least one of the tube contacting members is carried on its respective leg between the pair of inwardly extending members and the closed end of the body.

8. The device of claim 1 wherein the outer surface of said body is free of sharp ends and corners.

9. The device of claim 1 wherein said at least one opening in said body comprises an aperture enclosed by said body.

10. The device of claim 1 wherein the device does not include a releasing member for releasing said device from said irreversibly closed position.

11. The device of claim 1 wherein the pair of inwardly extending members on said other of said first and second legs comprises a spaced-apart solid walls defining a slot for receiving the inwardly extending member on said one of said first and second legs.

12. The device of claim 1 comprising two openings provided in said body for receiving a tubing segment therethrough.

13. The device of claim 12 wherein at least one of said openings in said body comprises an aperture enclosed by said body.

* * * * *